United States Patent [19]

Dove et al.

[11] Patent Number: 5,071,650

[45] Date of Patent: Dec. 10, 1991

[54] USE OF INTERMEDIATE LENGTH ALCOHOLS AS VIRUCIDAL AGENTS IN SOLUTIONS OF BIOLOGICALLY ACTIVE PROTEINS

[75] Inventors: George B. Dove, Hercules; Milton B. Dobkin, Lafayette; Michael A. Shearer, Fairfield, all of Calif.

[73] Assignee: Miles Inc., Elkhart, Ind.

[21] Appl. No.: 532,848

[22] Filed: Jun. 4, 1990

[51] Int. Cl.$^5$ .................... C07K 1/14; C07K 3/12
[52] U.S. Cl. .................... 424/85.8; 424/89; 424/93; 514/2; 514/21; 530/350; 530/364; 530/369; 530/380; 530/381; 530/382; 530/383; 530/384; 530/386; 530/387; 530/389; 530/410; 530/412; 530/424
[58] Field of Search .................... 424/89, 89.8, 93; 530/410, 412, 424, 380, 381, 383, 387, 389, 386, 362, 363, 382, 384, 364, 369, 350; 514/2, 21

[56] References Cited

U.S. PATENT DOCUMENTS 4,909,940  3/1990  Horowitz et al. .................... 424/531

OTHER PUBLICATIONS

Kurtz et al., J. Hosp. Infect. (England), vol. 1 (4), pp. 321-325 (1980).

Snipes et al., Antimicrob. Agents. Chemother of (U.S.A.), vol. 11 (1), pp. 98-104 (1977).

Primary Examiner—F. T. Moezie
Assistant Examiner—Andrew G. Rozycki
Attorney, Agent, or Firm—James A. Giblin

[57] ABSTRACT

Soluble, intermediate length alcohols ($C_4$–$C_{10}$) in aqueous solutions at low pH (4.0–7.0) can be used as virucidal agents for therapeutic biologically active protein preparations. Treatment with the alcohols is especially useful for proteins having activity not adversely affected by low pH.

12 Claims, 2 Drawing Sheets

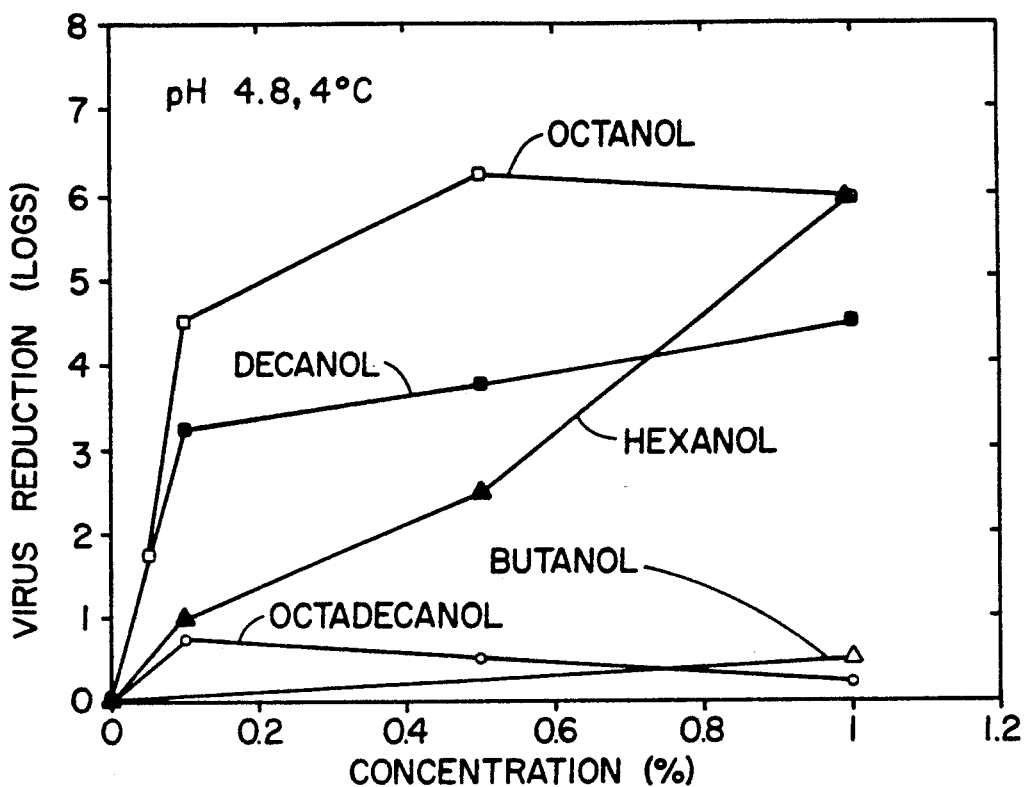
FIG._1.
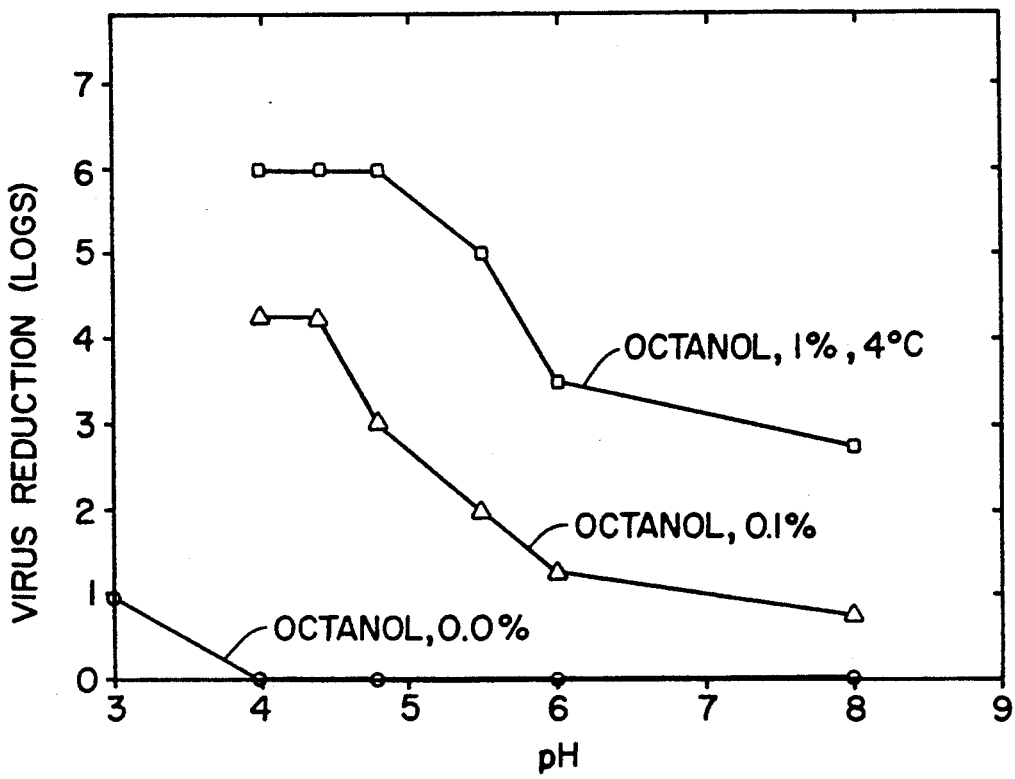
FIG._2.

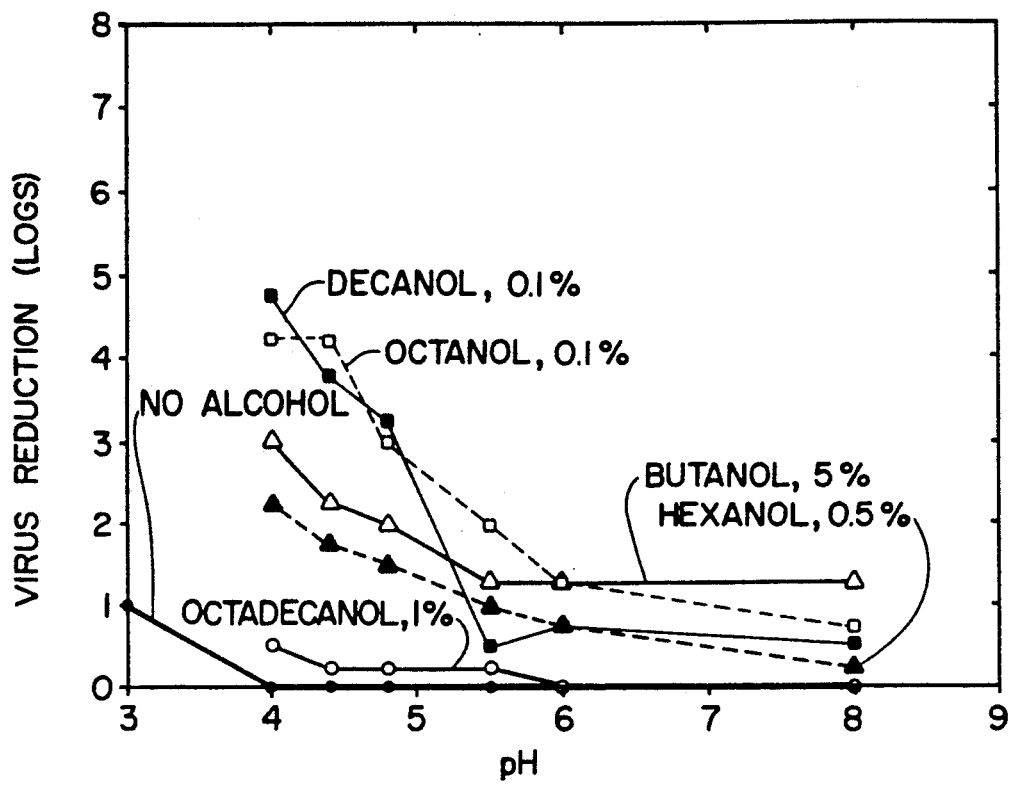
FIG._3.
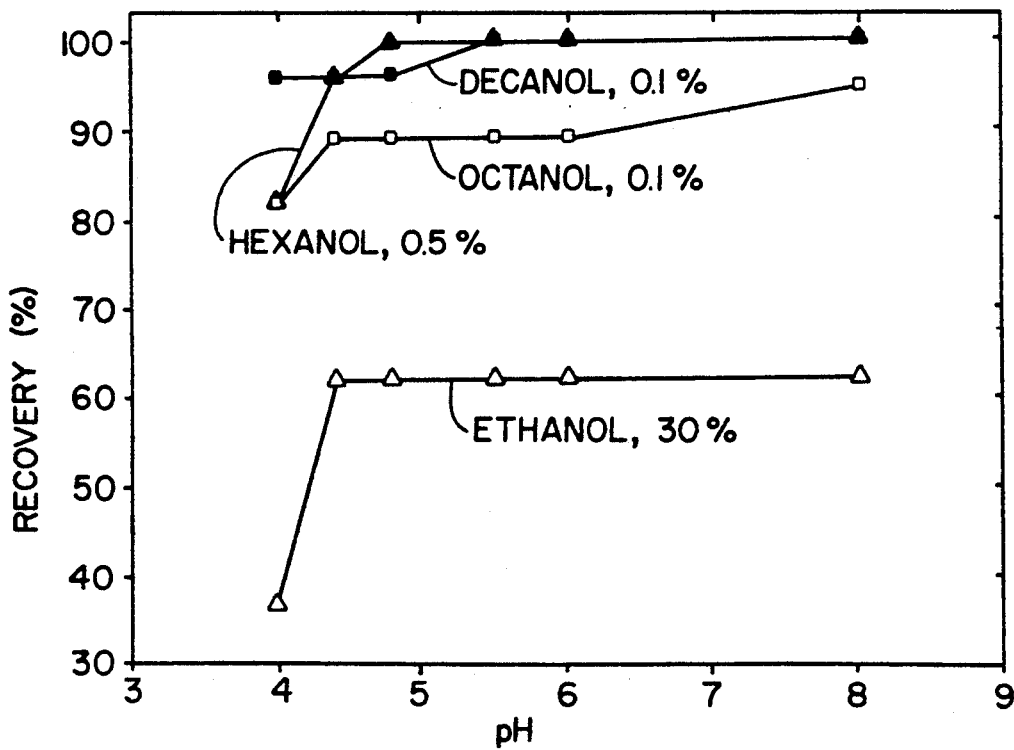
FIG._4.

USE OF INTERMEDIATE LENGTH ALCOHOLS AS VIRUCIDAL AGENTS IN SOLUTIONS OF BIOLOGICALLY ACTIVE PROTEINS

BACKGROUND OF THE INVENTION

1. Field

This disclosure is concerned generally with the use of alcohols as virucidal agents and is concerned specifically with the use of intermediate length alcohols to inactivate viruses in an aqueous solution of biologically active proteins.

2. Prior Art

The importance of eliminating viral infectivity in therapeutic products has long been recognized. This is especially true in the case of biologically active products derived from human blood or, more recently, from cell cultures used to make products of biotechnology (e.g. recombinant DNA products and monoclonal antibodies).

In considering virucidal agents for biologically active proteins, the primary goals are to assure complete virucidal action while not adversely affecting the biological activity of the protein. These goals require consideration of such variables as the protein itself, the nature of its activity and/or activity site, the virucidal agent, the importance and/or ease of its removal after use, and variables of the treatment itself, such as time, temperature, concentration, pH and ionic environment.

Although heat treatment alone can be used for virucidal treatment of some proteins (e.g. pasteurization conditions of at least 60° C. for at least 10 hours for albumin or pasteurization of lyophilized forms of some proteins such as factor VIII), it is difficult in many cases to avoid loss of biological activity or utility when heat alone is used.

Recent examples of the use of heat against viruses in a lyophilized biologically active product (dry heat treatment) can be seen in U.S. Pat. No. 4,556,558, to A. Rubenstein. The use of heat against viruses in a stabilized aqueous solution (wet heat treatment) can be found in U.S. Pat. No. 4,440,679, to P. Fernandez and J. Lundblad.

To avoid some of the disadvantages or activity losses resulting from the use of heat alone, various chemical agents have been used or proposed as virucidal agents for biologically active proteins. See for example, U.S. Pat. No. 4,540,573, to A. Neurath and B. Horowitz, disclosing the use of compounds such as tri-n-butyl phosphate (TNBP) as virucidal agents for protein products.

The use of certain alcohols (chain lengths carbons) to inactivate lipid-containing viruses is disclosed by W. Snipes et al in *Antimicrobial Agents and Chemotherapy*, "Inactivation of Lipid-Containing Viruses by Long Chain Alcohols", Vol. 11, No. 1, pp. 98-104, Jan. 1977. However, those studies were not concerned with preparations of biologically active proteins or the need to maintain the activity of such proteins. Although other alcohols were used, the authors suggest the use of alcohols that are extremely insoluble in aqueous media such as C10 to C14 alcohols. Because of the low water solubility, the preferred alcohols first had to be prepared in 95% ethanol at 100 times the desired final concentration. The final treatment was in solutions adjusted to a pH of at least 7.2. Although the authors used alcohols ranging from C4 to C18, they point out that a striking peak in virucidal activity was found for saturated alcohols having chain lengths from 10 to 14 carbons.

Although the $C_{10}$ - 14 alcohols were shown to have good virucidal action, their relatively low water solubility is a disadvantage in view of the initial preparation steps required. We have found this disadvantage can be avoided and that a class of alcohols can now be used to treat biologically active proteins under controlled pH conditions which in most cases has little adverse effect of biological activity. Details of our method and preferred embodiments are described below.

SUMMARY OF INVENTION

Our method of inactivating viruses in an aqueous solution of biologically active proteins comprises the step of treating the solution with a generally water soluble intermediate length alcohol having a carbon chain length of $C_4$ to $C_{10}$ at a pH below 7.0, preferably about 4.0 to 7.0 under conditions sufficient to eliminate substantially all virucidal infectivity (at least a 2 log reduction) without adversely affecting the biological activity of the protein. A very preferred treatment comprises contacting the solution of biologically active proteins with a saturated, straight chain alcohol such as octanol at a pH of about 4 to 5 for at least 1 minute at a temperature range of about to 80° C.

Two functional groups in the hydroxyl compounds are required for virus inactivation in aqueous solutions, namely a hydrophobic carbon group and a hydrophilic hydroxyl group. A chain length of eight carbons appears to be most virucidal. The lower solubility of the higher carbon chains may be a limiting factor. Monohydroxylic alcohols demonstrate highly virucidal properties compared with the corresponding alkane and diol derivatives. Especially in the lower pH range, substantial increases in virucidal activity occur with compounds that otherwise display only moderate inactivation under conditions of historical preference (i.e. physiological pH 7).

BRIEF DESCRIPTION OF THE FIGURES

FIG. 1 is a graph comparing VSV inactivation by various alcohols at varying concentrations at pH 4.8 and 4° C.

FIG. 2 is a graph comparing VSV inactivation by octanol varying octanol concentrations and pH.

FIG. 3 is a graph comparing VSV inactivation by a variety of alcohols at varying pH.

FIG. 4 is a graph showing the % recovery of IgM when treated with various alcohols at varying pHs.

SPECIFIC EMBODIMENTS

Classical techniques of virus inactivation utilizing heat or pH alone are often destructive to proteins in achieving the desired reduction of virus infectivity, giving less than 50% yield at times. The use of intermediate length alcohols disclosed here demonstrates relatively high virucidal activity against lipid-coated viruses over a broad range of pH while preserving biological activity. Historically, neutral pH has been utilized in processing and treatment to maintain protein stability. However, virus inactivation may be increased dramatically by treatment at lower pH. In specific instances, low yields (<50%) due to pH or the agent may be acceptable where the protein is labile or the requirements of virus inactivation are more stringent. The choice of virucidal compound and the conditions under which it is employed depends ultimately upon the requirements of virus inactivation and protein recovery.

MATERIALS AND METHODS

Chemical Agents

Saturated straight-chain alcohols with a terminal hydroxyl group (R-OH) ranging in carbon chain length from 2 to 18 were tested. Hexanol, octanol, and decanol were the six, eight and ten carbon homologs utilized predominantly, and are designated C6, C8, and C10, respectively. Ethanol served as a negative control under the conditions of this study.

Other eight-carbon compounds studied were 2-octanol, 1, 2 octanediol, 1, 8 octanediol, n-octane, and cis-3-octen-1-ol.

Compounds were reagent grade and obtained from Sigma Chemical, St. Louis, Mo. Protein solutions were buffered at the indicated pH with sodium acetate (J. T. Baker) and Tris base (Sigma).

Viruses

Vesicular stomatitis virus (VSV, a lipid-coated virus), Indiana strain, was obtained from the Finnish Red Cross and adapted to VERO cells.

Virus Assay

VSV was titrated under standard conditions on monolayers of VERO cells grown in 24 well plates using four wells per dilution.

Titers are expressed in terms of tissue culture infectious doses as a 50% end-point per mL (TCID$_{50}$/mL) (Karber, G. Arch. Exp. path. pharm. vol 162:480-3 (1931).

Buffers and Protein Solutions

Protein solutions were maintained with two buffer salts: sodium acetate at pH 4.0–8.0 and Tris and acetate at pH 8.0. The buffer consisted of 0.05M sodium acetate, 0.15M sodium chloride, pH as specified. Tris at 0.05M was present at pH 8.0.

Biologically active proteins from two sources (fermentation, plasma) were chosen as model systems to demonstrate wide virucidal activity. In the spectrum of proteins, antibodies demonstrated moderate stability over a wide range of conditions. Monoclonal (human) antibodies of class M (M-IgM, anti-Pseudomonas aeruginosa, cell lines ATCC Ascension No. CRL 8808, 8562, 8708, 8752, 8797) and monoclonal (human) antibodies of class G (anti-exotoxin A, cell line ATCC Ascension No. CRL 8833) were derived from Epstein-Barr virus-transformed human B lymphocytes grown in suspension culture or hollow fiber cartridges.

Factor VIII (FVIII), a coagulation factor required by hemophiliacs, was derived from recombinant baby hamster kidney cells grown in suspension culture.

Several proteins derived from plasma were tested. Alpha-1 proteinase inhibitor (a1PI or antitrypsin) inhibits the enzymatic cleavage of elastin to elastase. α1PI was isolated from Fraction IV-1 of the Cohn-Oncley plasma fractionation process. Similarly, human serum albumin was isolated from Fraction V.

Except where noted, the protein concentration in the examples below was 0.5 mg/ml.

Protein stability was evaluated by A$_{280}$, radial immunodiffusion, and FPLC-Superose 6 (Pharmacia Fast Protein Liquid Chromatography employing high performance size exclusion). Alpha-1 proteinase inhibitor was assayed for biological activity by competitive assay with elastase (Coan MH, Brockway WJ, Eguizabel H, Krieg T, Fournel M. Vox. Sang. 48, 333, 1985). Factor VIII was assayed by a modified method of Langdell (Langdell RD, Wagner RH, Brinkhouse A. "Effect of Anti-Hemophiliac Factor on One-Stage Clotting Test," J Lab Clin Med 41: 637-647, 1953) based on activated partial thromboplastin time (APTT).

Experimental Design

Evaluation of virucidal efficacy was carried out in two stages First, a concentration profile was established at pH 4.8. The ranges of pH and concentration were chosen for process considerations. The choices proved to be fortuitous in demonstrating virucidal efficacy as a function of pH, contrary to historical preference for physiological conditions (e.g. pH 7).

The concentrations of the alcohols ranged from 0.05-1.0% (v/v for the C$_4$ to C$_{10}$ alcohols or w/v for C$_{12}$ and greater alcohols), except where noted otherwise. From this, a single concentration demonstrating a 3–4 log reduction in viral infectivity was then selected for the second stage of the evaluation, in which a profile from pH 4.0 to 8.0 was completed.

RESULTS: VIRUS INACTIVATION

Alcohol Homologs

As noted earlier, infectivity of VSV (a lipid-coated virus) is not affected by pH 4–8 alone in these buffers for at least 2 hours, the longest incubation time reported.

To determine the concentration of alcohol that would reduce the infectivity of VSV approximately 3–4 logs at pH 4.8, homologs (C2–C18) were combined with 0.05% IgM solution as described in Materials and Methods. The results of this experiment, shown in FIG. 1 and Table 1, indicate that heptanol (C7), octanol (C8), and nonanol (C9) are the most virucidal of the alcohols on a weight basis, depending on the specific concentration being examined at pH 4.8.

The data in FIG. 1 indicate that octanol completely inactivates VSV (approximately 6 logs) at concentrations above 0.5%. From C2 to C8, the alcohols demonstrate increasing virus inactivation with increasing concentration. The plot appears to be linear with octanol. A plateau is apparent at higher concentrations because the virus assay and titer are limiting. Less than 1 log (TCID50/ml) is not detectable; the maximum virus titer available is 7-8 logs. Therefore, the maximum measurable inactivation is 6-7 logs. With C9 or greater, the alcohols exhibit a biphasic curve. The increase in virus reduction is greater between 0 and 0.1% than between 0.1% and 1%. However, there appears to be no hyperbolic tendency, as is often observed with a time or concentration plot.

TABLE 1

Effect of Alcohol Concentration and Carbon Chain Length (C4–C10) on Inactivation of VSV in 0.05% Albumin, pH 4.8, at 4° C. for 60 minutes.

| Conc. (%) | Carbon Chain Length | | | | | | |
|---|---|---|---|---|---|---|---|
|  | C4 | C5 | C6 | C7 | C8 | C9 | C10 |
| None | 0 | 0 | 0 | 0 | 0 | 0 | 0 |
| 0.05 | 0 | 0 | 0 | 0 | 1.75 | 4.0 | — |
| 0.1 | 0 | 0 | 0 | 1.25 | 4.5 | 4.5 | 3.25 |
| 0.5 | 0 | 0 | 2.5 | >6.5 | 6.25 | 5.0 | 3.75 |
| 1.0 | 0 | 1.5 | >6.0 | — | >6.0 | 5.0 | 4.5 |
| 5.0 | 2.75* | >6.0 | — | — | — | — | — |

TABLE 1-continued

Effect of Alcohol Concentration and Carbon Chain Length (C4–C10) on Inactivation of VSV in 0.05% Albumin, pH 4.8, at 4° C. for 60 minutes.

| Conc. (%) | Carbon Chain Length | | | | | | |
|---|---|---|---|---|---|---|---|
| | C4 | C5 | C6 | C7 | C8 | C9 | C10 |
| 10 | >6.25 | — | — | — | — | — | — |
| 20 | — | — | — | — | — | — | — |
| 30 | — | — | — | — | — | — | — |
| 40 | — | — | — | — | — | — | — |

*Reduction in virus titer (log 10).
— Not tested

In contrast, incubation with 30% ethanol at pH 4.8 results in 1.75 log reduction at 4° C.

As stated previously in Materials and Methods, the concentration of alcohol for use in the pH profile was extremely important, since either too large or too small a level would not permit the pH effect to be observed over the entire pH range under the specified limitations (1 hr., 4° C.). The effects of concentrations were indicated by preliminary experiments that produced the pattern shown in FIG. 2.

The highest concentration of octanol demonstrated moderate kill at the higher pH, but the trend at lower pH is obscured by complete viral inactivation (see earlier comments on virus assay and titer). Concentrations above do not result in substantially greater inactivation compared to 1% (discussed later). A concentration of 0.1%, however, demonstrates a consistent decline throughout the entire pH range (pH 4 to 8). The plots appear to be parallel in slope, reflecting only the difference in alcohol concentration. Extending the range below pH 4 or above pH 10 would result in virus inactivation due to pH alone.

Having obtained, where possible, the level for each alcohol resulting in a 3–4 log inactivation of VSV at pH 4.8, a pH profile was carried out with each alcohol between pH 4.0 and 8.0, as shown in FIG. 3. Consistent with all homologs, the tendency for increased viral inactivation with decreasing pH is seen. If the compound is virucidal at a suitably high concentration, the incremental effect of pH is great, as demonstrated by a steep slope. For example, butanol at 5%, hexanol at 0.5% and octanol at 0.1% give similar patterns. However, the higher alcohols (C12 and above) show less dramatic results over-all as would be expected by the lower inactivation in FIG. 1.

Comparison of Compounds with the Same Chain Length

A series of different eight carbon compounds was studied to determine the effects of the monopole (terminal hydroxyl group) on virucidal activity and the effects of an unsaturated carbon chain (in addition to the effect of length). Table 2 shows virus titers after treatment for 30 and 60 minutes.

TABLE 2

Inactivation Kinetics of VSV in 0.05% Albumin Containing Various C8 Compounds at pH 4.8, 4° C. for 60 minutes

| Compound | Conc. (%) | Time (minutes) | | |
|---|---|---|---|---|
| | | 30 pH 4.8 | 60 pH 4.8 | 60 pH 8 |
| 1-octanol | 0.1 | — | >4.5 | 0.75 |
| | 1.0 | >6.0* | >6.0 | 2.75 |
| 2-octanol | 1.0 | 4.25 | 4.75 | — |
| 1,2 octanediol | 1.0 | 4.25 | 5.25 | 3.50 |
| 1,8-octanediol | 1.0 | 1.25 | 2.0 | 0.0 |
| n-octane | 1.0 | 0.25 | 0.75 | 0.25 |
| cis-3-octen-1-ol | 1.0 | 5.75 | >6.0 | — |

*Reduction in virus titer (log 10).
— Not tested

The highly virucidal nature of 1-octanol and the relative lack of activity of the alkane indicates the critical importance of the position of the functional hydroxyl group.

Movement of the hydroxyl group to the 2 position (2-octanol) or addition of a second hydroxyl group at the same end (1,2-octanediol) diminishes virucidal activity moderately compared to 1-octanol at the same concentration. Addition of a hydroxyl group to the opposite end (1,8-octanediol) markedly reduced the virucidal activity to a level only slightly greater than that of the alkane.

The effect of unsaturated carbon chains was observed with cis-3-octen-1-ol. The unsaturated alcohol demonstrated less virucidal activity than 1-octanol, but slightly greater than 2-octanol and 1,2 octanediol. The effectiveness of the single polar group as a function of pH can be seen in Table 2. Common to all compounds, lower pH enhanced virucidal activity. As observed previously in FIG. 3, the effect of pH is most apparent in those compounds demonstrating moderate or high virucidal qualities at pH 4.8.

ADDITIONAL FACTORS

Protein Load: Varying levels of albumin were tested with 0.1% octanol. Virus inactivation is reduced by increasing protein load (Table 3). Substitution of albumin for IgM in several of the previous experiments yielded identical results.

Temperature/Time: High virucidal activity occurs with increased temperature and time intervals. For example, 0.1% octanol at pH 4.8 gives 3 and 6 logs reduction at 4 and 20° C., respectively, at 0.5 hours. After 1 hour, 5 and 6 logs reduction are observed, respectively.

TABLE 3

Effect of Protein Concentration on Virus Inactivation at pH 4.4, 4° C. for 6 min.

| Albumin concn. (%) | Reduction in VSV titer (log 10) |
|---|---|
| 5 | 0.25 |
| 0.5 | 3.25 |
| 0.05 | 4.75 |

Results: Protein Recovery

Studies with various biologically active proteins were conducted. Variation of parameters and the resulting protein recovery data followed the same strategy previously presented for the virus inactivation experiments. For comparison of compounds, concentrations were chosen in an effort to relate virucidal efficiency and protein recovery.

Monoclonal IgM, line ATCC 8752

The effects of alcohol concentration on protein recovery were observed by treating aqueous solutions of IgM at pH 4.8 with alcohol homologs (C2–C18), as described in Materials and Methods. The results of this experiment are shown in Table 4 and may be compared to FIG. 1, where virus inactivation increases steadily with C2–C8 and plateaus at 0.1% for C9 or greater.

Ethanol displays the expected pattern of reduced yield with increasing concentration. In the case of alcohols other than ethanol, protein recovery is quantitative at concentrations greater than 0.1%. Reduced yields are observed at lower concentrations of the C6–C10 alcohols. The C12 and higher alcohols give quantitative recovery. This pattern is similar to virus inactivation in this low concentration range, where C8–C10 were most virucidal. The loss in yield associated with C6 does not correspond with significant virucidal activity.

RECOVERY OF PROTEINS

TABLE 4

Effect of Alcohol Concentration on Recovery of IgM at pH 4.8, 4° C. Yields are expressed as a percentage of the untreated control.

| Agent | Concentration (%) | | | | |
|---|---|---|---|---|---|
| | 0 | 10 | 30 | 40 | 60 |
| C2 | 100 | 90 | 62 | 49 | 0 |

| Agent | Concentration (%) | | | | |
|---|---|---|---|---|---|
| | 0.02 | 0.05 | 0.1 | 0.5 | 1 |
| C6 | | 82 | 100 | 100 | 100 |
| C8 | 100 | 82 | 89 | 100 | 100 |
| C10 | | 68 | 96 | 100 | 100 |

Further definition of the dependency of concentration is shown in Table 5, analogous to the strategy for FIG. 2. Recovery does not appear to demonstrate the same critical dependency on pH that virus inactivation exhibits.

TABLE 5

Effect of pH on Recovery of IgM (in Octanol) at 4° C. Yields are expressed as a percentage of the untreated control.

| Conc. (%) | pH | | | | | |
|---|---|---|---|---|---|---|
| | 4 | 4.4 | 4.8 | 5.5 | 6 | 8 |
| 0.1 | 82 | 89 | 89 | 89 | 89 | 95 |
| 1 | 100 | 93 | 100 | 96 | 100 | 100 |

The effect of pH on protein recovery was determined with each alcohol between pH 4.0 and 8.0, as shown in Table 6 and FIG. 4. The tendency for increased protein recovery with increasing pH is observed, with low yields occurring only below pH 4.4. Extending the range below pH 4 or above pH 10 would result in loss of yield due to pH alone.

TABLE 6

Effect of pH on Recovery of IgM in Alcohols at 4° C. Yields are expressed as a percentage of the untreated control.

| Agent | Conc. (%) | pH | | | | | |
|---|---|---|---|---|---|---|---|
| | | 4 | 4.4 | 4.8 | 5.5 | 6 | 8 |
| C2 | 30 | 37 | 62 | 62 | 62 | 62 | 62 |
| C6 | 0.5 | 82 | 96 | 100 | 100 | 100 | 100 |
| C8 | 0.1 | 82 | 89 | 89 | 89 | 89 | 95 |
| C10 | 0.1 | 96 | 96 | 96 | 100 | 100 | 100 |

Analysis of the data obtained with various C8 compounds (Table 7) demonstrates greater recovery effected by the monohydroxylic alcohol compared to other compounds. The alkane was found to be exceptionally destructive to IgM, giving no recovery even at the lowest concentration. 2-octanol and 1,2-octanediol are comparable to 1-octanol in recovery. 1,8-octanediol is relatively destructive and is obtained with cis-3-octen-1-ol. Lower yields associated with low concentrations are yield loss ameliorated by higher pH, higher temperatures and the presence of stabilizing proteins (albumin at 0.1%). As solubility may be limiting, temperature becomes a factor affecting more than temperature-dependent degradation kinetics.

TABLE 7

Effect of Various C8 Compounds on Recovery of IgM at 4° C. Yields are expressed as a percentage of the untreated control.

| Agent | Conc. (%) | pH | | | | | |
|---|---|---|---|---|---|---|---|
| | | 4 | 4.4 | 4.8 | 5.5 | 6 | 8 |
| 1-octanol (c8) | 0.1 | 82 | 89 | 89 | 89 | 89 | 95 |
| | 1 | 100 | — | 100 | — | — | 100 |
| n-octane | 0.1 | 0 | — | 0 | — | — | 0 |
| 2-octanol | 1 | 89 | — | 96 | — | — | 96 |
| 1,2-octanediol | 1 | 100 | — | 100 | — | — | 96 |
| 1,8-octanediol | 1 | 55 | — | 82 | — | — | 96 |
| cis-3-octen-1-ol | 0.1 | 62 | — | 89 | — | — | 82 |
| cis-3-octen-1-ol | 1 | — | — | 78 | — | — | — |

COMPARISON WITH OTHER MONOCLONAL ANTIBODIES

Various monoclonal IgM preparations (m-IgM) demonstrate different stabilities in these solvents. The m-IgM utilized most frequently in this study (line 8752) is relatively stable compared to several other m-IgMs that demonstrate greater aggregate formation and subsequent loss of activity. Table 8 shows the lower stability of IgMs with lines 8808 and 8708, compared to 8752. This relative instability occurs over a wide range of conditions. IgGs exhibit higher stability in a variety of conditions (unpublished observations). Exposure to alcohols follows this tendency. At pH 4.0–8.0, concentrations of octanol exceeding 1% may be used without significant loss (Table 8).

TABLE 8

Effect of Octanol Concentration and pH on Recovery of IgM and IgG at 4° C. Yields are expressed as a percentage of the untreated control.

| Conc. (%) | pH | Yield (%):Aggregation (%)* | | | |
|---|---|---|---|---|---|
| | | IgM Line 8752 | IgM Line 8708 | IgM Line 8808 | IgG Line 8833 |
| 0.1 | 4.8 | 89:1 | 89:2 | 75:4 | 100:<1 |
| 0.1 | 8 | 95:1 | 95:2 | 80:2 | 100:<1 |
| 1 | 4.8 | 100:2 | 20:>5 | — | 95:2 |

*Analysis by FPLC

Factor VIII

Factor VIII is a fairly labile protein which tolerates pH 6–8 under most conditions. Recovery at pH 6.5 in the presence of octanol is shown in Table 9, demonstrating high recovery to 1% octanol.

TABLE 9

Effect of Concentration on Recovery of FVIII in Octanol at 4° C. and pH 7.0. Yields are expressed as a percentage of the untreated control.

| Octanol Conc. (%) | Yield (%) |
|---|---|
| — | 100 |
| 0.05 | 92 |
| 0.1 | 90 |
| 1.0 | 90 |

Plasma-derived Proteins

Alpha-1 proteinase inhibitor (alPI) tolerates pH 5.1-8.0. Recoveries in the presence of several alcohols, shown in Table , are high at pH 6-8 and moderate below pH 6.

TABLE 10

Effect of Concentration and pH on recovery of alPI in Alcohols at 4° C. Yields are expressed as a percentage of the untreated control.

| Agent | Conc. (%) | pH 4 | 4.4 | 4.8 | 5.5 | 6 | 8 |
|---|---|---|---|---|---|---|---|
| None | | 10 | 10 | 50 | 90 | 100 | 100 |
| C6 | 1.0 | — | — | — | 70 | 80 | 80 |
| C8 | 0.1 | — | — | — | 60 | 75 | 90 |
| C8 | 1.0 | — | — | — | 60 | — | — |

Recovery of albumin in these alcohols is essentially quantitative. The protein appears to be unaffected by C6, C8, C10 and C12 at concentrations up to 1% at all pH.

Discussion

The single most significant finding in this work is that intermediate chain saturated alcohols demonstrate pH-dependent virucidal activity. In addition to pH, concentration affects the level of viral inactivation in relation to the physical properties of the compound (i.e., solubility). In general, solubility decrease chain length increases or the number of hydrophilic groups decreases. The monocarboxylic alcohols demonstrate a four-fold reduction in solubility with the addition of each carbon.

Virucidal activity was shown to increase with increasing carbon chain length up to C8. Above C8 viral inactivation continued at high levels in the presence of relatively low concentrations of alcohols. With increasing concentration, however, virucidal activity became limited, compared to C6 and C8 compounds. Insolubility of the larger chain compounds might be expected to create an absolute plateau of effectiveness at relatively low concentrations. This expectation is not supported entirely by experiments as demonstrated in FIG. 1, where a biphasic pattern is seen for decanol and dodecanol. Although the concentrations are in excess of their saturation, a plateau does not occur. In fact, increasing effectiveness was shown up to 10 times the saturation concentration and no effect was obtained at 1/10 saturation.

Functional dependency was further defined by the relative absence of virucidal effectiveness associated with progressive disruption of the monopole. Thus, where one polar group (i.e. hydroxyl) was attached terminally to 8 carbons and showed highly efficient viral inactivation, the movement of the hydroxyl group to the 2 position (2-octanol) reduced the monopole effect and virucidal activity moderately. Addition of a second hydroxyl group at the same end (1,2-octanediol) diminished the monopole effect compared to 1-octanol. The activities of 1-octanol and 1,2-octanediol are similar, indicating that the 2-hydroxyl group masks the significant effect of the 1-hydroxyl group. Addition of a hydroxyl group to the opposite end (1,8-octanediol) eliminated any monopole effect and reduced severely the virucidal activity to only slightly greater than that of the alkane (Table 2). The diols possess greater solubility than either the alcohols or alkanes (Table 5), indicating that solubility is but one of multiple criteria for virus inactivation.

These findings suggest that a single polar group and non-polar chain interact with the virus coat to effectively disrupt the membrane. It is hypothesized that the carbon chain is entwined in the lipid coat and the polar group allows interaction with water. A micelle effect is established which is not possible with the alkane or the di-hydroxyl group. Critical micelle size (alcohol CMC) may be a factor in exposing the virus to sufficient reagent in the solution or in interactions with the virus particle. Alternatively, the optimization of eight carbons may be dependent on the virus itself. The coat thickness may allow maximum disruption with a length of eight carbons.

Finally, proteins may adsorb the agent, reducing the effective concentration and consequent virus inactivation. Therefore, application to various protein solutions depends on the protein species present.

In alcohols, the dependency of protein recovery on pH is not as dramatic as the effects of pH on virus inactivation. A decline in yield is observed only at pH 4.0, and occasionally, at pH 4.4. The remainder of the range exhibits no distinct pattern. The lower yields at the lower concentrations of 0.05-0.1% had been observed with other compounds near their saturation points discrepancy in yield may be caused by micelle formation at higher concentrations, leading to protein stabilization. Virus inactivation appears to increase as a function of concentration beyond the solubility point, suggesting the possibility that micelle formation results in partition of the virus rather than inactivation.

Given the above disclosure it is thought numerous variations will occur to those skilled in the art. Accordingly, it is intended that the above examples should be construed as illustrative and that the invention disclosed herein should be limited only by the following claims.

We claim:

1. A method of inactivating viruses in a aqueous solution of biologically active proteins selected from the group consisting of antibodies, coagulation factors, albumin and protease inhibitors, the method comprising the step of contacting the solution with a $C_4$ through $C_{10}$ alcohol at a pH ranging from about 4.0 to 7.0 and under conditions sufficient to result in a substantial viral inactivation without adversely affecting the biological activity of the protein.

2. The method of claim 1 wherein the alcohol is 1-octanol.

3. The method of claim 1 wherein the viruses are lipid-coated viruses.

4. The method of claim 1 wherein the product is a therapeutic protein.

5. The method of claim 1 wherein the substantial inactivation of viruses amounts to a reduction of greater than 99% of the original virus titer in the product.

6. The method of claim 5 wherein the contact with the alcohol results in a loss of less than 50% of the original biological activity of the protein.

7. The method of claim 6 wherein the alcohol is 1-octanol and the contact is at a pH ranging from about 4.0 to about 5.0.

8. The method of claim 7 wherein the protein is expressed from a cell culture.

9. The method of claim 8 wherein the protein is expressed from a genetically altered cell line.

10. A method of inactivating lipid-coated viruses in an aqueous solution of therapeutic, biologically active proteins selected from the group consisting of antibodies, coagulation factors, albumin and protease inhibitors, the method comprising the step of contacting the solution with 1-octanol at a pH ranging from about 4.0 to about 5.0 under conditions sufficient to result in substantial inactivation of viruses without adversely affecting the biological activity of the proteins.

11. The method of claim 10 wherein the contact with the 1-octanol results in a loss of less than 50% of the original biological activity of the proteins.

12. The method of claim 10 wherein the substantial inactivation of viruses amounts to a reduction of greater than 99% of the original virus titer in the product.

* * * * *